United States Patent
Neumann

(10) Patent No.: US 11,948,683 B2
(45) Date of Patent: Apr. 2, 2024

(54) METHOD FOR PROVIDING A SECONDARY PARAMETER, DECISION SUPPORT SYSTEM, COMPUTER-READABLE MEDIUM AND COMPUTER PROGRAM PRODUCT

(71) Applicant: Siemens Healthcare GmbH, Erlangen (DE)

(72) Inventor: Dominik Neumann, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 1406 days.

(21) Appl. No.: 16/005,863

(22) Filed: Jun. 12, 2018

(65) Prior Publication Data

US 2018/0366224 A1    Dec. 20, 2018

(30) Foreign Application Priority Data

Jun. 14, 2017  (EP) .................................... 17176007

(51) Int. Cl.
*G06N 20/00* (2019.01)
*G06N 3/042* (2023.01)
(Continued)

(52) U.S. Cl.
CPC .............. *G16H 50/20* (2018.01); *G06N 3/042* (2023.01); *G06N 3/045* (2023.01); *G06N 3/08* (2013.01);
(Continued)

(58) Field of Classification Search
CPC ...... G16H 50/20; G16H 30/40; G06N 3/0454; G06N 3/08; G06N 20/00; G06N 3/02
See application file for complete search history.

(56) References Cited

U.S. PATENT DOCUMENTS 6,873,718 B2   3/2005 O'Donnell et al.
8,116,548 B2   2/2012 Zheng et al.
(Continued)

FOREIGN PATENT DOCUMENTS

CN   104331600 A   2/2015
CN   104866727 A   8/2015
(Continued)

OTHER PUBLICATIONS

Heimann T, Meinzer HP. Statistical shape models for 3D medical image segmentation: a review. Medical image analysis. Aug. 1, 2009;13(4):543-63. (Year: 2009).*
(Continued)

*Primary Examiner* — Oluwatosin O Alabi
(74) *Attorney, Agent, or Firm* — Harness, Dickey & Pierce, P.L.C.

(57) ABSTRACT

A method for providing a secondary parameter, a decision support system, a computer-readable medium and a computer program product are disclosed. In an embodiment, the method is for providing a secondary parameter in a decision support system providing a primary parameter, in particular in a clinical decision support system. The method includes: providing an input data set; approximating a secondary parameter based on the input data set by using a sub-system being trained by a machine learning mechanism, in particular by a deep learning mechanism; and providing the approximated secondary parameter. The input data set is a shape data set.

22 Claims, 3 Drawing Sheets

(51) Int. Cl.
| | |
|---|---|
| *G06N 3/045* | (2023.01) |
| *G06N 3/08* | (2023.01) |
| *G06N 5/048* | (2023.01) |
| *G16H 30/40* | (2018.01) |
| *G16H 50/20* | (2018.01) |
| *G16H 50/30* | (2018.01) |
| *G16H 50/70* | (2018.01) |
| *G06N 3/02* | (2006.01) |

(52) U.S. Cl.
CPC ............ *G06N 5/048* (2013.01); *G06N 20/00* (2019.01); *G16H 30/40* (2018.01); *G16H 50/30* (2018.01); *G16H 50/70* (2018.01); *G06N 3/02* (2013.01)

(56) References Cited

U.S. PATENT DOCUMENTS

| | | | |
|---|---|---|---|
| 8,396,533 | B2 | 3/2013 | Barbu et al. |
| 9,025,841 | B2 | 5/2015 | Wels et al. |
| 10,962,939 | B1* | 3/2021 | Das ................... G06T 7/277 |
| 2012/0041318 | A1 | 2/2012 | Taylor |
| 2013/0338496 | A1* | 12/2013 | Hielscher ............ A61B 5/0064 600/425 |
| 2014/0073976 | A1* | 3/2014 | Fonte ................. A61B 6/5217 600/504 |
| 2014/0257804 | A1* | 9/2014 | Li ...................... G10L 15/16 704/232 |
| 2015/0112182 | A1* | 4/2015 | Sharma .............. A61B 5/7264 600/408 |
| 2015/0238148 | A1* | 8/2015 | Georgescu ........... G06T 7/0012 600/408 |
| 2016/0106321 | A1* | 4/2016 | Sharma .............. A61B 6/507 600/407 |
| 2016/0129282 | A1 | 5/2016 | Yin et al. |
| 2016/0129637 | A1* | 5/2016 | Zhou .................. G05B 15/02 700/98 |
| 2016/0188824 | A1 | 6/2016 | Geleijnse et al. |
| 2016/0196384 | A1 | 7/2016 | Mansi et al. |
| 2017/0018075 | A1 | 1/2017 | Middlebrooks et al. |
| 2017/0071671 | A1 | 3/2017 | Neumann et al. |
| 2017/0076451 | A1 | 3/2017 | Pauly |
| 2017/0113002 | A1 | 4/2017 | Shanechi |
| 2017/0270663 | A1* | 9/2017 | Hoffmann ............. G06T 17/20 |
| 2017/0304732 | A1* | 10/2017 | Velic ................... G06V 20/66 |
| 2018/0000339 | A1* | 1/2018 | Hipsley .............. G16H 20/40 |
| 2018/0018553 | A1* | 1/2018 | Bach .................. G06F 40/279 |
| 2018/0068083 | A1* | 3/2018 | Cohen ................ G16B 50/30 |
| 2018/0137941 | A1 | 5/2018 | Chen |
| 2018/0144466 | A1* | 5/2018 | Hsieh ................. G06T 7/0012 |
| 2018/0322660 | A1* | 11/2018 | Smith ................. G06K 9/6267 |

FOREIGN PATENT DOCUMENTS

| | | | |
|---|---|---|---|
| CN | 105431851 | A | 3/2016 |
| CN | 106529116 | A | 3/2017 |
| CN | 106778005 | A | 5/2017 |
| EP | 3270308 | A1 * | 1/2018 ............ G06N 20/00 |

OTHER PUBLICATIONS

Su H, Maji S, Kalogerakis E, Learned-Miller E. Multi-view convolutional neural networks for 3d shape recognition. InProceedings of the IEEE international conference on computer vision 2015 (pp. 945-953). (Year: 2015).*

Pfitzner C, May S, Nuchter A. Neural network-based visual body weight estimation for drug dosage finding. InMedical Imaging 2016: Image Processing Mar. 21, 2016 (vol. 9784, pp. 524-532). SPIE. (Year: 2016).*

Ogunyemi O. Methods for reasoning from geometry about anatomic structures injured by penetrating trauma. Journal of biomedical informatics. Aug. 1, 2006;39(4):389-400. (Year: 2006).*

Masci, Jonathan et al.: "ShapeNet: Convolutional Neural Networks on Non-Euclidean Manifolds", Feb. 2, 2015, XP055415559, pp. 1-13; 2015.

Schmidhuber, Jürgen: "Deep Learning in Neural Networks: An Overview" Technical Report IDSIA-03-14, vol. 61, Jan. 31, 2015, pp. 1-88.

Itu, Lucian et al. "A Machine Learning Approach for Computation of Fractional Flow—Reserve from Coronary Computed Tomography"; in: J Appl Physiol; 2016; DOI 10.1152/japplphysiol.00752. 2015.; 2016.

Masci, Jonathan et al.: "Geodesic convolutional neural networks on Riemannian manifolds", in: arXiv:1501.06297v2 [cs.CV]; Nov. 19, 2015; pp. 1-9.

Extended European Search Report #17176007.7 dated Nov. 8, 2017.

Itu, Lucian, et al. "A machine-learning approach for computation of fractional flow reserve from coronary computed tomography." Journal of Applied Physiology 121.1 (2016): 42-52.; 2016.

European Office Action dated Dec. 21, 2018.

Kutz, J. Nathan "Deep learning in fluid dynamics" Journal of Fluid Mechanics, vol. 814, Jan. 31, 2017 (Jan. 31, 2017), ISSN: 0022-1120, https://doi.org/10.1017/jfm.2016.803 // DOI: 10.1017/jfm. 2016.803; 2017.

Tompson, Jonathan et al. "Accelerating Eulerian Fluid Simulation With Convolutional Networks" arXiv:1607.03597 [cs.CV], 2016.

Wikipedia "Machine learning" Retrieved from the Internet: URL: https://en.wikipedia.org/w/index.php?; 2017.

European Office Action dated Aug. 6, 2018.

Chinese Office Action and English translation thereof dated Sep. 13, 2021.

Chinese Office Action and English translation thereof dated Mar. 11, 2021.

V. Thanachartwet et al. Dynamic Measurement of Hemodynamic Parameters and Cardia Preload in Adults with Dengue: A Prospective Observational Study, *PLOS one*, 2016, pp. 1-17.

* cited by examiner

METHOD FOR PROVIDING A SECONDARY PARAMETER, DECISION SUPPORT SYSTEM, COMPUTER-READABLE MEDIUM AND COMPUTER PROGRAM PRODUCT

PRIORITY STATEMENT

The present application hereby claims priority under 35 U.S.C. § 119 to European patent application number EP17176007.4 filed Jun. 14, 2017, the entire contents of which are hereby incorporated herein by reference.

FIELD

At least one embodiment of the present invention generally describes a method for providing a secondary parameter, a decision support system, a computer-readable medium and/or a computer program product.

BACKGROUND

Clinical decision support (CDS) systems are essential tools that assist clinicians in their complex decision making process, by providing them relevant patent-specific information. Such information might be for example image data sets, lab reports or general data such as the age of the patient. By accumulating and filtering the relevant information the CDS system helps to make a diagnostic or therapeutic decision.

SUMMARY

The inventors have realized, however, that some relevant information are not available for the CDS system, since their calculation is complex and time-consuming, such that the information cannot be made available in a comparatively short time. For example, a pressure and/or a blood flow velocity is such an information. For calculation of these quantities typically a computational fluid dynamics simulation is needed and therefore these information cannot be made available in an appropriate time.

At least one embodiment of the present invention provides an additional information, i.e. a secondary parameter, fast and uncomplicatedly to a decision support system, in particular to a clinical decision support system.

At least one embodiment of the present invention is directed to a method for providing a secondary parameter; a decision support system; a computer program product and the a computer readable medium.

According to a first embodiment of the present invention, a method for providing a secondary parameter in a decision support system, in particular in a clinical decision support system, that supplies a primary parameter to a user, is provided, comprising:

providing an input data set;

approximating an secondary parameter based on the input data set by using a sub-system being trained by a machine learning mechanism, in particular by a deep learning mechanism; and providing the approximated secondary parameter; wherein the input data set is a shape data set.

Another embodiment of the present invention is directed to a decision support system, in particular a clinical decision support system, wherein the decision support system is configured for performing a method according to an embodiment of the present invention.

Another embodiment of the present invention is directed to a computer program product for carrying out the steps of the method according to at least one embodiment of the present invention.

Another embodiment of the present invention is directed to a computer-readable medium on which is stored a program element that can be read and executed by a computed unit in order to perform steps of the method according to an embodiment of the present invention, when the program elements are executed by the computer unit.

Further advantages and features will emerge from the following description of example embodiments of the method for analyzing according to the invention with reference to the accompanying drawings. Individual features of the individual embodiments can be combined with one another here within the scope of the invention.

DETAILED DESCRIPTION OF THE EXAMPLE EMBODIMENTS

Figure 1:
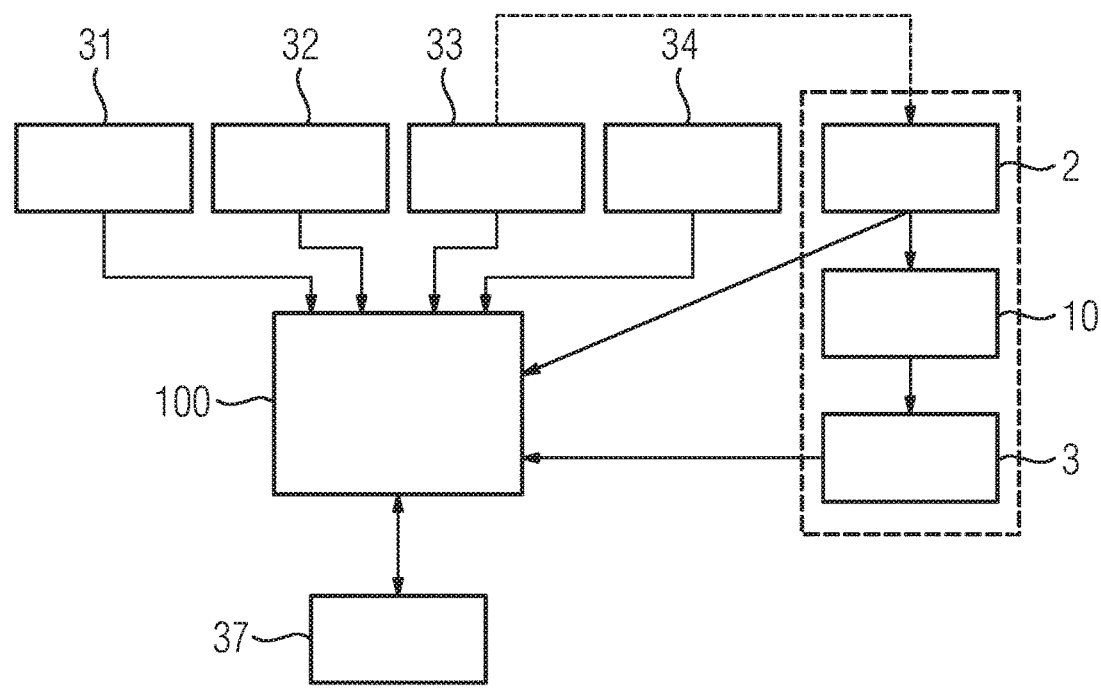
FIG. 1 shows schematically a block diagram illustrating an example embodiment of a method for providing a secondary parameter according to an example embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Nonlimiting examples of the non-transitory computer-readable medium include, but are not limited to, rewriteable nonvolatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable nonvolatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment of the present invention, a method for providing a secondary parameter in a decision support system, in particular in a clinical decision support system, that supplies a primary parameter to a user, is provided, comprising:

providing an input data set;

approximating an secondary parameter based on the input data set by using a sub-system being trained by a machine learning mechanism, in particular by a deep learning mechanism; and providing the approximated secondary parameter;

wherein the input data set is a shape data set.

In contrast to the state of the art, a shape data set is used as an input for a sub-system being trained by a machine learning mechanism. As a consequence, the decision support system can be extended and improved to facilitate decision-making by providing the additional information, i.e. the secondary parameter, derived from shape data sets. By using the trained sub-system, it is possible to perform only a forward pass for approximating the secondary parameter. That means the second parameter can be provided in a comparatively short time without computationally expensive calculations. By reducing the computational demand for providing the secondary parameter, it is further advantageously possible to reduce hardware requirements of the CDS system.

In general, the trained sub-system is an artificial neuronal network, in particular trained by a deep learning mechanism. Preferably, the sub-system comprises a processor being configured for approximating the secondary parameter based on the input data set and being configured for being trainable by a machine learning mechanism, in particular by a deep learning mechanism. Further, it is preferably provided, that the trained sub-system comprises an input layer for receiving the input data set, a plurality of hidden layers and an output layer for providing the secondary parameter.

Primary parameters are preferably information being stored in a memory device such as patient information, for example a patient age or BMI, an image data set such as MR or CT image data set, lab reports, for example blood tests and/or medical knowledge. Preferably, the CDS system is configured such that it accumulates and filters the available primary parameter for displaying the relevant data to the user, for example a clinician, for assisting the decision making process.

The term "shape data set" preferably describes data sets that can be represented by any kind of polygonal mesh. For example the data set comprises a set of vertices, triangles and/or polygons that form two dimensional (2D) or three dimensional (3D) meshes. It is also thinkable, that the shape data set comprises volumetric meshes formed from vertices, tetrahedra, hexahedra or other three dimensional elements. Preferably, the shape data set comprises a segmentation of a surface of a three dimensional object, in particular an organ or structure in a body, wherein the surface is derived from an image data set. For example, the shape data set is extracted from an image data set showing a three dimensional object of the patient.

The term "secondary parameters" preferably describes parameters that can be derived from the shape data set, in particular can be calculated as a function of the shape data set. For example, a liver volume is a secondary parameter that can be derived, in particular calculated, from a shape of the surface of the liver. According to another example, the second parameter is a hemodynamic parameter, such a pressure or a blood velocity inside a vessel, at a given point of time and might be calculated by a computational fluid dynamic (CFD) solver, wherein a surface mesh of the vessel is used as input for the CFD solver.

In particular, it is provided that the approximation by the sub-system trained by the machine learning mechanism replaces a calculation that is usually used, such for example a computational fluid dynamic solution. Preferably, the approximated secondary parameter is provided by displaying the second parameter on a display device such as a screen of a workstation or a screen of a mobile unit, such as a tablet or smart phone. In particular the CDS system displays the approximated parameter together with the primary parameters.

Further advantageous embodiments and features of the invention are given by the claims, as revealed in the following description. Feature of different claim categories may be combined as appropriate to give further embodiments not described herein.

According to an example embodiment, it is provided that the shape data set is extracted, preferable automatically extracted, from primary parameters being available to the decision support system. For example an image data set associated to a three dimensional object is part of the primary parameters. By transforming at least a part of the image data set to a corresponding shape data set, which for example associated to a surface of the three dimensional object, the shape data set is extracted. Thus, it is advantageously possible to use the primary parameters being available to the decision support system for approximating secondary parameter. It is also thinkable, that the extracted shape data set is transferred to the set of primary parameters. Thus, the user can check whether an approximation of the secondary parameter is based on a valid extraction of the shape data set. Preferably, the term "automatically" indicates that another sub-system is trained by another machine learning mechanism for selecting the proper subset of primary information for providing the shape data set as an input data set.

In an example embodiment, it is provided that the shape data set is extracted from a subset of the image data set, for example a specific patch of the three-dimensional image data set. As a consequence, a reduced amount of data can be used for approximating the secondary parameter. In particular, sub-sets of the image data set being irrelevant for approximating the secondary parameter are not used as an input for the trained sub-system.

Preferably, it is provided, that the sub-system being trained comprises an input layer, a plurality of hidden layers and an output layer. In particular, the sub-system is configured for receiving shape data sets and the output layer provides the secondary parameter to the user, for example by displaying the secondary parameter on a screen. Thereby the input layer, the plurality of hidden layers and the output layer are part of an artificial neuronal network, wherein neurons of the neuronal network can be weighted or connected to each other during the training process.

According to an example embodiment, it is provided that the shape data set is prepared for providing it to the input layer. By preparing the shape data set it is advantageously possible to establish a link between the shape data set and the input layer of the trained sub-system. In particular, it is also thinkable that a feature, for example in form of a shape descriptor or a spectral descriptor, is calculated from at least a subset of the shape data set and provided to the input layer.

In an example embodiment the shape data set is prepared by sampling. For example, an extension of conventional neural networks to non-Euclidean manifolds, such as shapes, is used for preparing the shape data set. The extension of conventional neural networks to non-Euclidean manifolds is described by Masci et al. in the article "ShapeNet: Convolutional Neuronal Networks on Non-Euclidean Manifolds" in EPFL-CINF-204949, 2015. Relating to the extension of conventional neural networks to non-Euclidean manifolds the description explicitly refers hereby to this document.

In another example embodiment, it is provided that the shape data set is transformed to an intermediate image data set for providing the intermediate image data set to the input layer. In particular, it is provided that the shape data set is transformed to an intermediate image data set being compatible with a standard deep learning algorithm. As a consequence, the deep learning mechanism has not to be adapted to the form of the shape data set. For example, a shape data set could be converted to a binary mask or a level-set representation. By using a binary mask discrete voxel values are provided, for example 0 for outside and 1 for inside, whereas by a level-set representation continuous voxel values encoding a distance of voxel to a boundary are provided.

In particular, it is provided that the trained subsystem has more than 5 hidden layers, preferably more than 10 hidden layers. By using a high number of hidden layers the sub-system is trainable by a deep learning mechanism. In particular, it is possible to predict secondary parameters having a complex dependency on the shape-data by using a high number of hidden layers.

According to a further embodiment, it is provided that the secondary parameter is provided while the decision support system is running. Thus, the secondary parameter can be approximated on the fly and be immediately provided to the user. It is also thinkable that the user can select, whether he wants to be informed about the second parameter or not. For example, the approximation of the secondary parameter starts, when the user requests the second parameter.

In another example embodiment, it is provided that the secondary parameter is provided together with at least one primary parameter. In particular, the secondary parameter advantageously supplements the primary parameters. It is also conceivable that the decision support system filters the secondary parameter. For example the decision support system provides the secondary parameters to the user only, when the secondary parameter corresponds to a value within a set interval. Thus, the user might be warned by a secondary parameter, when the value of the secondary parameter indicates an abnormality.

Preferably, it is provided, that in an offline mode the sub-system is trained by a plurality of training shape data sets. By training the sub-system the quality of approximating the secondary parameter is improved. Thereby, it is thinkable that at least several training shape data sets are generated artificially. In particular, it is provided, that in the offline mode the training shape data set is provided and an approximated second parameter is provided by the sub-system to be trained. By comparing the approximated value to a real value of the secondary parameter, it is possible to adapt the sub-system such that a discrepancy between the approximated second parameter and the real second parameter is minimized. Thus a trained sub-system can be provided. The real second parameter might be a measured value or a value being the result of an exact calculation, for example by a computation fluid dynamics solver.

In another embodiment, it is provided that in the offline mode, the second parameter is calculated. In particular, the second parameter is calculated on-the-fly, i.e. during the training of the subsystem.

Another embodiment of the present invention is directed to a decision support system, in particular a clinical decision support system, wherein the decision support system is configured for performing a method according to an embodiment of the present invention.

Another embodiment of the present invention is directed to a computer program product for carrying out the steps of the method according to at least one embodiment of the present invention.

Another embodiment of the present invention is directed to a computer-readable medium on which is stored a program element that can be read and executed by a computed unit in order to perform steps of the method according to an embodiment of the present invention, when the program elements are executed by the computer unit.

Further advantages and features will emerge from the following description of example embodiments of the method for analyzing according to the invention with reference to the accompanying drawings. Individual features of the individual embodiments can be combined with one another here within the scope of the invention.

In FIG. 1 an example embodiment of a method for providing an additional information according to an example embodiment is schematically shown. Preferably, the method is part of a clinical decision support system 100 (CDS). Such a clinical decision support 100 system is configured such that it collects primary parameters 31, 32, 33, 34 and presents them to a user, for example on a screen of a workstation or a mobile unit such as a tablet or smartphone. The presented primary parameter 31, 32, 33, 34 support the user making a decision, for example whether a patient is operable or not. Primary parameter 31, 32, 33, 34 are preferably information being stored in a memory device such as patient information 31, for example a patient age or BMI, an image data set 33 such as MR or CT image data set, lab reports 32, for example blood tests and/or medical knowledge 34. Preferably the CDS system 100 is configured such that it accumulates and filters the available primary parameter 31, 32, 33, 34 for displaying the relevant information for assisting the decision making process.

In particular, a second parameter 3 is provided in addition to the primary parameters 31, 32, 33, 34 by the method according to the embodiment in FIG. 1. Secondary parameters 3 depend for example on a shape of an organ and are relevant for the decision making process. For example, a second parameter 3 is a liver volume that depends on a shape of the liver being represented by an image data set. Preferably, the second parameter 3 cannot be provided such easily as a liver volume. For example, a calculated secondary parameter 37, such as a computational fluid dynamics (CFD) solution, is needed for providing the secondary parameter 3, wherein the shape is used as input for a CFD solver. Secondary parameters 3 might be a pressure or a blood flow velocity in a vessel.

For providing the secondary parameter 3 to the CDS system 100 the secondary parameter 3 is approximated by a sub-system 10 trained by a machine learning mechanism. Thereby, a shape data set 2 is used as an input data set for the sub-system 10. Preferably, the shape data set 2 is extracted from the primary parameters 31, 32, 33, 34 being available in the CDS system 100. For example, the shape data set 2 is extracted from an image data set 33. A shape data set 2 is a data set that can be represented by any kind of polygonal mesh, in particular 2D and 3D surface meshes or volumetric meshes.

Figure 2:
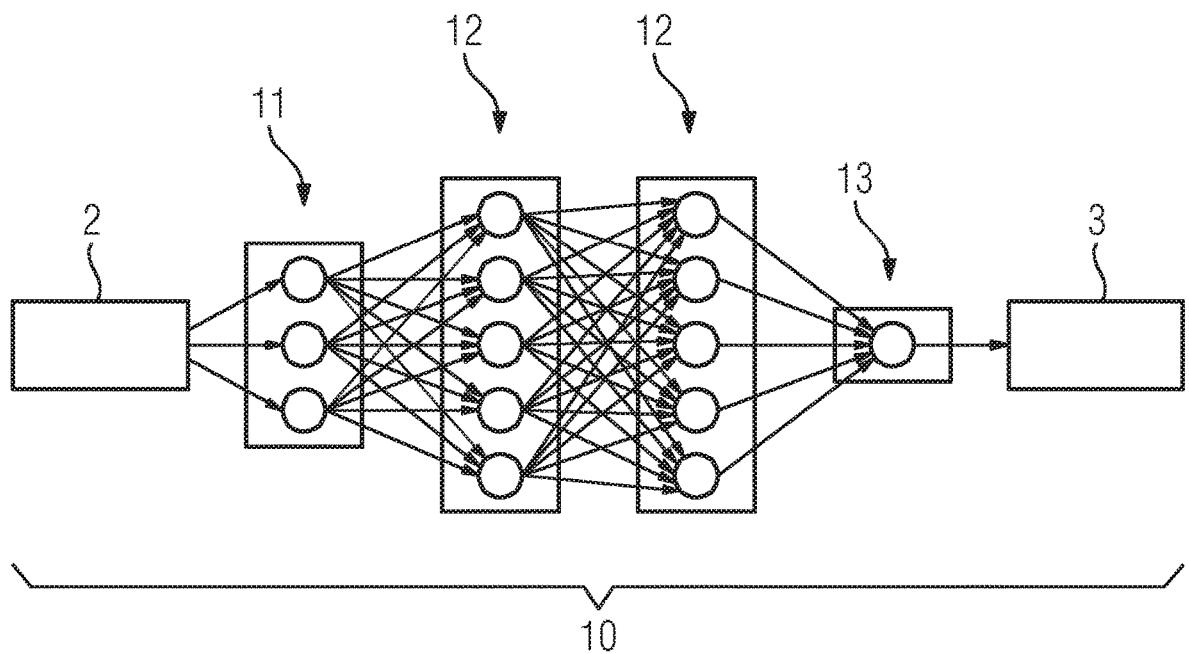
FIG. 2 shows schematically a block diagram illustrating a sub-system being trained by a machine learning mechanism for a method according to an example embodiment.

FIG. 2 schematically shows a sub-system 10 being trained with a machine learning mechanism. In particular, the sub-system 10 is an artificial neuronal network and the machine learning mechanism is a deep learning mechanism. The sub-system 10 preferably comprises an input layer 11 and an output layer 13. In addition to the input layer 11 and the output layer 13 the sub-system 10 further has several hidden layers 12. Thereby the input layer 11 is configured for receiving a shape data set 2 and the output layer 13 is configured for providing the secondary parameter 3. By training the sub-system 10 learns to handle the input data set and to predict an output corresponding to the secondary parameter 3. Thereby, the relevance of individual neurons of the artificial neuronal network might be weighted and connections between neuron of different hidden layers 12 might be generated during the training.

Figure 3:
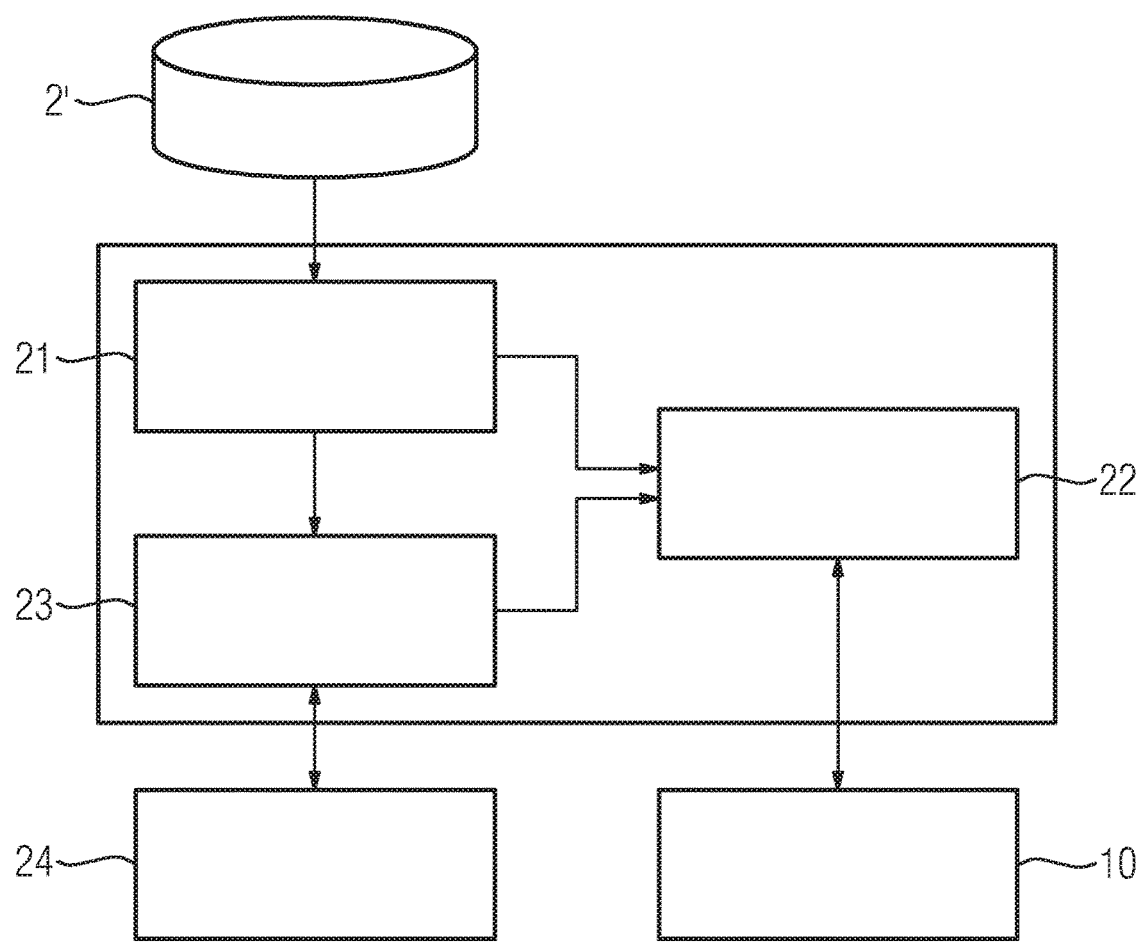
FIG. 3 shows schematically a block diagram illustrating a training of a sub-system and FIG. 4 shows an aorta (left) and a block diagram illustrating a shape data set for incorporating into the input layer (right).

In FIG. 3 a training of a sub-system 10 is schematically shown. In particular, in the beginning a training shape data set 2' is provided. Such a training shape data set 2' might be extracted from a real image data set 33 or an artificial generated image data set 33. It is also thinkable that the training shape data 2' set is generated artificially for training the sub-system 10. Based on the training data set 2' an approximated secondary parameter 3 is provided by the sub-system 10 and compared to the real secondary parameter 3 in a first step 21. The real secondary parameter 3 might be the result of a measurement or of a complex calculation of a user-defined function 24 in a second step 22. Subsequently, the sub-system 10 is adapted for minimizing the difference/error between the approximated secondary parameter 3 and the real secondary parameter 3 in a third step 23. By iterating the approximation and the adapting of the sub-system 10 a trained sub-system 10 is provided, in particular a trained deep shape network. It is also thinkable, that the calculation of the user-defined function is performed during the training, i.e. on-the-fly, for example by a CFD solver. As a consequence of the training the trained sub-system 10 provides a secondary parameter 3 on basis of the shape data set 2 without the need of time consuming computationally expensive calculations.

Figure 4:
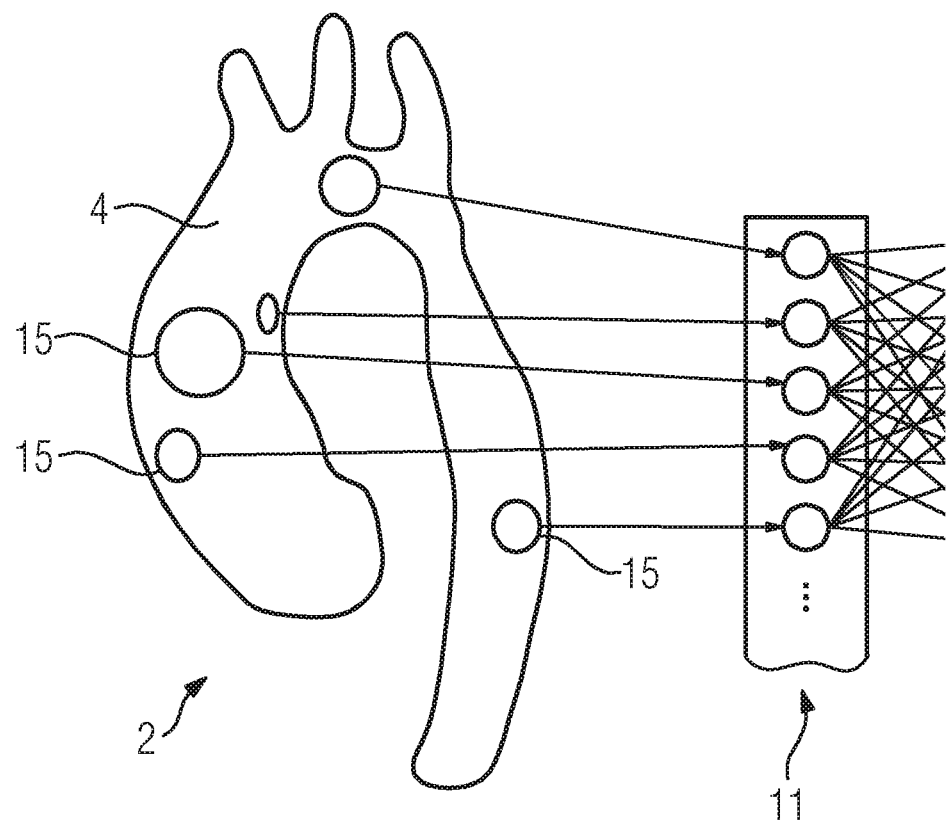

In FIG. 4 a three dimensional shape data set 2 is illustrated. The three dimensional image data set 33 shows an aorta 4, wherein the shape data set 2 is provided as a triangulated mesh. In particular, a sampling of the shape data set 2 is illustrated. By sampling, the shape data set 2 is prepared for incorporating the shape data set 2 into the trained sub-system 10, in particular into the input layer 11. Preferably, patches of the three dimensional object are extracted/analysed and the corresponding shape data set 2 is provided to the trained sub-system 10.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing a secondary parameter in a decision support system to supply at least one primary parameter to a user, the method comprising:
   generating a polygonal mesh indicating a shape data set of the at least one primary parameter;
   providing the polygonal mesh, as an input data set, to a subsystem, the subsystem being trained by a machine learning algorithm;
   approximating, by the sub-system, the secondary parameter based on the polygonal mesh, the secondary parameter being at least one of a hemodynamic parameter or a liver volume, and the secondary parameter being generated from a shape of the shape data set indicated by the polygonal mesh; and
   providing the secondary parameter.

2. The method of claim 1, wherein the at least one primary parameter includes at least one of a plurality of primary parameters, and the shape data set is extracted from the plurality of primary parameters available to the decision support system.

3. The method of claim 2, wherein the shape data set is extracted from a subset of an image data set.

4. The method of claim 2, wherein the shape data set is automatically extracted from the plurality of primary parameters available to the decision support system.

5. The method of claim 1, wherein the sub-system includes an input layer, a plurality of hidden layers and an output layer.

6. The method of claim 5, wherein the shape data set is prepared for providing the polygonal mesh to the input layer.

7. The method of claim 6, wherein the shape data set is prepared by sampling.

8. The method of claim 6, further comprising:
training the shape data set to an intermediate image data set; and
providing the intermediate image data set to the input layer.

9. The method of claim 5, further comprising:
transforming the shape data set to an intermediate image data set; and
providing the intermediate image data set to the input layer.

10. The method of claim 1, wherein the sub-system includes more than 5 hidden layers.

11. The method of claim 10, wherein the sub-system includes more than 10 hidden layers.

12. The method of claim 1, wherein the secondary parameter is provided while the decision support system is running.

13. The method of claim 1, wherein the secondary parameter is provided together with the at least one primary parameter.

14. The method of claim 1, further comprising:
training the sub-system based on a plurality of training shape data sets in an offline mode.

15. The method of claim 14, further comprising:
calculating the secondary parameter in the offline mode.

16. A decision support system, configured for performing the method of claim 1.

17. A device for providing a secondary parameter in a decision support system to supply a primary parameter to a user, the device comprising:
one or more processors; and
a memory storing executable instructions that, when executed by the one or more processors, cause the one or more processors to perform the method of claim 1.

18. A non-transitory computer-readable medium, storing executable instructions that, when executed, cause a processor to perform the method of claim 1.

19. The method of claim 1, wherein the decision support system is a clinical decision support system.

20. The method of claim 1, wherein the machine learning mechanism is a deep learning mechanism.

21. The method of claim 1, wherein the sub-system is trained by the machine learning mechanism to minimize an error between a calculated hemodynamic parameter and an approximated hemodynamic parameter to approximate the hemodynamic parameter, the calculated hemodynamic parameter being calculated via a computational fluid dynamics solver.

22. The method of claim 1, wherein the hemodynamic parameter includes at least one of heart rate, blood pressure, stroke volume, cardiac output, or total peripheral resistance.

* * * * *